(12) United States Patent
Martin

(10) Patent No.: US 6,201,574 B1
(45) Date of Patent: Mar. 13, 2001

(54) MOTIONLESS CAMERA ORIENTATION SYSTEM DISTORTION CORRECTING SENSING ELEMENT

(75) Inventor: H. Lee Martin, Knoxville, TN (US)

(73) Assignee: Interactive Pictures Corporation, Knoxville, TN (US)

(*) Notice: Subject to any disclaimer, the term of this patent is extended or adjusted under 35 U.S.C. 154(b) by 0 days.

(21) Appl. No.: 08/795,005

(22) Filed: Feb. 5, 1997

Related U.S. Application Data

(63) Continuation of application No. 08/761,876, filed on Dec. 9, 1996, now abandoned, which is a continuation-in-part of application No. 08/373,446, filed on Jan. 17, 1995, which is a continuation-in-part of application No. 08/189,585, filed on Jan. 31, 1994, now Pat. No. 5,384,588, which is a continuation-in-part of application No. 08/014,508, filed on Feb. 8, 1993, now Pat. No. 5,359,363, which is a continuation-in-part of application No. 07/699,366, filed on May 13, 1991, now Pat. No. 5,185,667.

(51) Int. Cl.[7] .................................................. H04N 5/225

(52) U.S. Cl. ........................... 348/315; 348/335; 348/36; 348/143

(58) Field of Search ................................ 348/36, 43, 44, 348/39, 46, 147, 143, 332, 340, 315, 335, 342, 294, 311, 91; 382/293–298; 395/137–139; 250/208.1, 206.2; 702/3; 73/170.16; H04N 5/30, 5/225

(56) References Cited

U.S. PATENT DOCUMENTS

| | | | |
|---|---|---|---|
| 3,351,763 | * 11/1967 | Shuart | .................................. 348/332 |
| 3,723,805 | 3/1973 | Scarpino et al. | ................. 315/27 GD |
| 4,125,862 | 11/1978 | Catano | ................................. 358/140 |

(List continued on next page.)

FOREIGN PATENT DOCUMENTS 2-127877 5/1990 (JP).
WO 82/03712 10/1982 (WO).

OTHER PUBLICATIONS

English Abstract 2–127877 (A), May 16, 1990, for "Electronic Still Camera Provided With Fisheye Lens" Japanese Application No. 63–281550.
Suzanne Oliver, "Fooling the Eye", Forbes, p. 94, Jan. 16, 1995.
Deposition of Richard J. Felix, Nov. 9, 2000.
Exhibit 4 –"The Omnigraph, Omnidirectional Spherical Photography" and "Omnigraphics, second report," Richard J. Felix, 1970's.

(List continued on next page.)

Primary Examiner—Michael Lee
(74) Attorney, Agent, or Firm—Banner & Witcoff, Ltd.

(57) ABSTRACT

A device for omnidirectional image viewing providing pan-and-tilt orientation, rotation, and magnification within a hemispherical field-of-view that utilizes no moving parts. The imaging device is based on the effect that the image from a fisheye lens, which produces a circular image of an entire hemispherical field-of-view, can be mathematically corrected using high-speed electronic circuitry. More specifically, an incoming fisheye image is captured on a Charge Coupled Diode array in such a way as to remove the distortion caused by the lens by locating the picture pickup elements in a nonlinear manner described herein. As a result, this device can accomplish the functions of pan, tilt, rotation, and zoom throughout a hemispherical field-of-view without the need for any mechanical mechanisms. The preferred embodiment of the image capture device can provide corrected images at standard video frame rates, compatible with standard video equipment. The device can be used for aiming the video device in any application where a conventional pan-and-tilt or orientation mechanism might be considered including inspection, monitoring, surveillance, video teleconferencing, and target acquisition.

36 Claims, 5 Drawing Sheets

U.S. PATENT DOCUMENTS

| | | | |
|---|---|---|---|
| 4,152,724 | 5/1979 | Hunter | 358/109 |
| 4,191,967 | 3/1980 | Dansac et al. | 358/113 |
| 4,463,380 | 7/1984 | Hooks, Jr. | 358/160 |
| 4,467,361 * | 8/1984 | Ohno et al. | 348/340 |
| 4,518,898 | 5/1985 | Tarnowski et al. | 315/371 |
| 4,549,208 | 10/1985 | Kamejima et al. | 358/108 |
| 4,661,855 | 4/1987 | Gulck | 358/225 |
| 4,670,648 | 6/1987 | Hall et al. | 250/216 |
| 4,728,839 | 3/1988 | Coughlan et al. | 310/112 |
| 4,751,660 | 6/1988 | Hedley | 364/518 |
| 4,772,942 | 9/1988 | Tuck | 358/87 |
| 4,835,532 | 5/1989 | Fant | 340/728 |
| 4,858,002 | 8/1989 | Zobel | 358/98 |
| 4,858,149 | 8/1989 | Quarendon | 364/522 |
| 4,914,284 * | 4/1990 | Halldorsson et al. | 250/206.3 |
| 4,918,473 | 4/1990 | Blackshear | 354/81 |
| 4,924,094 | 5/1990 | Moore | 250/334 |
| 4,945,367 | 7/1990 | Blackshear | 354/81 |
| 4,965,844 | 10/1990 | Oka et al. | 382/44 |
| 4,991,020 | 2/1991 | Zwirn | 358/160 |
| 5,005,083 | 4/1991 | Grage et al. | 358/181 |
| 5,020,114 | 5/1991 | Fujioka et al. | 382/44 |
| 5,023,725 | 6/1991 | McCutchen | 358/231 |
| 5,048,102 | 9/1991 | Tararine et al. | 382/41 |
| 5,067,019 | 11/1991 | Juday et al. | 358/160 |
| 5,068,735 | 11/1991 | Tuchiya et al. | 358/209 |
| 5,173,948 | 12/1992 | Blackham et al. | 382/44 |
| 5,185,667 | 2/1993 | Zimmermann | 358/209 |
| 5,200,818 | 4/1993 | Neta et al. | 358/87 |
| 5,231,673 | 7/1993 | Elenga | 382/6 |

OTHER PUBLICATIONS

Exhibits 6, 26, 29, 30, 32–35 –Omnigraphics course materials, California State University –Richard J. Felix –1974 to 1994.

Exhibits 17 –"Multiplex Video Display", Richard J. Felix, Feb. 7, 1994.

* cited by examiner

MOTIONLESS CAMERA ORIENTATION SYSTEM DISTORTION CORRECTING SENSING ELEMENT

This application is a continuation of U.S. application Ser. No. 08/761,876 filed Dec. 9, 1996, now abandoned which is a continuation-in-part of U.S. application Ser. No. 08/373,446.filed Jan. 17, 1995, which is a continuation-in-part of U.S. application Ser. No. 08/189,585 filed Jan. 31, 1994, now U.S. Pat. No. 5,384,588, which is a continuation-in-part of U.S. application Ser. No. 08/014,508 filed Feb. 8, 1993, now U.S. Pat. No. 5,359,363, which is a continuation-in-part of U.S. application Ser. No. 07/699,366 filed May 13, 1991, now U.S. Pat. No. 5,185,667.

TECHNICAL FIELD

The invention relates to an apparatus and algorithm for transforming a hemispherical field-of-view image into a non-distorted, normal perspective image at any orientation, rotation, and magnification within the field-of-view. The viewing direction, orientation, and magnification are controlled by either computer or remote control means. More particularly, this apparatus is the electronic equivalent of a mechanical pan, tilt, zoom, and rotation camera viewing system with no moving mechanisms. It relates to previous patent U.S. Pat. No. 5,185,667 by implementation of the distortion correction using a specialized physical layout of the elements that convert light to electrical charge.

BACKGROUND ART

Camera viewing systems are utilized in abundance for surveillance, inspection, security, and remote sensing. Remote viewing is critical for robotic manipulation tasks. Close viewing is necessary for detailed manipulation tasks while wide-angle viewing aids positioning of the robotic system to avoid collisions with the workspace. The majority of these systems use either a fixed-mount camera with a limited viewing field, or they utilize mechanical pan-and-tilt platforms and mechanized zoom lenses to orient the camera and magnify its image. In the applications where orientation of the camera and magnification of its image are required, the mechanical solution is large and can subtend a significant volume making the viewing system difficult to conceal or use in close quarters. Several cameras are usually necessary to provide wide-angle viewing of the workspace.

In order to provide a maximum amount of viewing coverage or subtended angle, mechanical pan/tilt mechanisms usually use motorized drives and gear mechanisms to manipulate the vertical and horizontal orientation. An example of such a device is shown in U.S. Pat. No. 4,728,839 issued to J. B. Coughlan, et al, on Mar. 1, 1988. Collisions with the working environment caused by these mechanical pan/tilt orientation mechanisms can damage both the camera and the worksite and impede the remote handling operation. Simultaneously, viewing in said remote environments is extremely important to the performance of in-on and manipulation activities.

Camera viewing systems that use internal optics to provide wide viewing angles have also been developed in order to minimize the size and volume of the camera and the intrusion into the viewing area. These systems rely on the movement of either a mirror or prism to change the tilt-angle of orientation and provide mechanical rotation of the entire camera to change the pitch angle of orientation. Using this means, the size of the camera orientation system can be minimized, but "blind spots" in the center of the view result Also, these systems typically have no means of magnifying the image and or producing multiple images from a single camera.

Accordingly, it is an object of the present invention to provide an apparatus that can provide an image of any portion of the viewing space within a hemispherical field-of-view without moving the apparatus.

It is another object of the present invention to provide horizontal orientaton (pan) of the viewing direction with no moving mechanisms.

It is another object of the present invention to provide vertical orientaton (tilt) of the viewing direction with no moving mechanisms.

It is another object of the present invention to provide rotational orientaton (rotation) of the viewing direction with no moving mechanisms.

It is another object of the present invention to provide the ability to magnify or scale the image (zoom in and out) electronically.

It is another object of the present invention to provide electronic control of the image intensity (iris level).

It is another object of the present invention to be able to change the image intensity (iris level) without any mechanisms.

It is another object of the present invention to be able to accomplish said pan, tilt, zoom, rotation, and iris with simple inputs made by a lay person from a joystick, keyboard controller, or computer controlled means.

It is also an object of the present invention to provide accurate control of the absolute viewing direction and orientations using said input devices.

A further object of the present invention is to provide the ability to produce multiple images with different orientations and magnifications simultaneously.

A further object of this invention is to embed the image correction algorithm in the physical image sensing electronic component placement on the picture elements on the Charge Coupled Device (CCD) video sensor.

A further object of the invention is to be able to scan the CCD element by direct addressing of the individual CCD picture elements in any order during the scan using the CCD array in a manner similar to addressable video memory.

Another object of the present invention is to be able to provide these images at real-time video rates, that is 30 transformed images per second, and to support various display format standards such as the National Television Standards Committee RS-170 display formal These and other objects of the present invention will become apparent upon consideration of the drawings hereinafter in combination with a complete description thereof.

DISCLOSURE OF THE INVENTION

In accordance with the present invention, there is provided an omnidirectional viewing system that produces the equivalent of pan, tilt, and zoom within a hemispherical field-of-view with no moving parts. This device includes a means for converting light energy into electronic charges commonly referred to as a charge coupled device (CCD) geometrically arranged in a non-standard pattern so as to remove the distortion associated with a specific lens configuration. The geometric arrangement is described by the equations developed within this patent. This device also includes a means to selectively scan the CCD so that the entire CCD need not be scanned to generate an image. The selective scanning of the device allows the CCD array to support a much larger number of elements than are typical of standard resolution systems by scanning only the elements in the region of interest as selected by an external input. In one preferred embodiment, the incoming image is produced by a fisheye lens which has a hemispherical field-of-view. This hemispherical field-of-view image is captured into the special CCD array. A portion of the captured image containing a region-of-interest is scanned by the associated electronics to create an output image. The viewing orientation is designated by a command signal generated by either a human operator or computerized input The transformed image is deposited in a second electronic memory buffer where it is then manipulated to produce the output image as requested by the command signal.

BEST MODE FOR CARRYING OUT THE INVENTION

In order to minimize the size of the camera orientation system while maintaining the ability to zoom, a camera orientation system that utilizes electronic image transformations rather than mechanisms was developed. While numerous patents on mechanical pan-and-tilt systems have been filed, to our knowledge, only our previous patent, U.S. Pat. No. 5,185,667 developed by Dr. H. Lee Martin and S. D. Zimmermann of TRI deals with the electronic implementation of pan, tilt, rotation, and magnification of a video image. In addition, the electro-optical approach utilized in the present invention allows multiple images to be extracted from the output of a single camera.

Motivation for this device came from viewing system requirements in remote handling applications where the operating envelope of the equipment is a significant constraint to task accomplishment The device has application for robotic remote viewing, medical endoscopy, security and surveillance, remote vehicle operation, video teleconferencing and interactive video.

Figure 1:
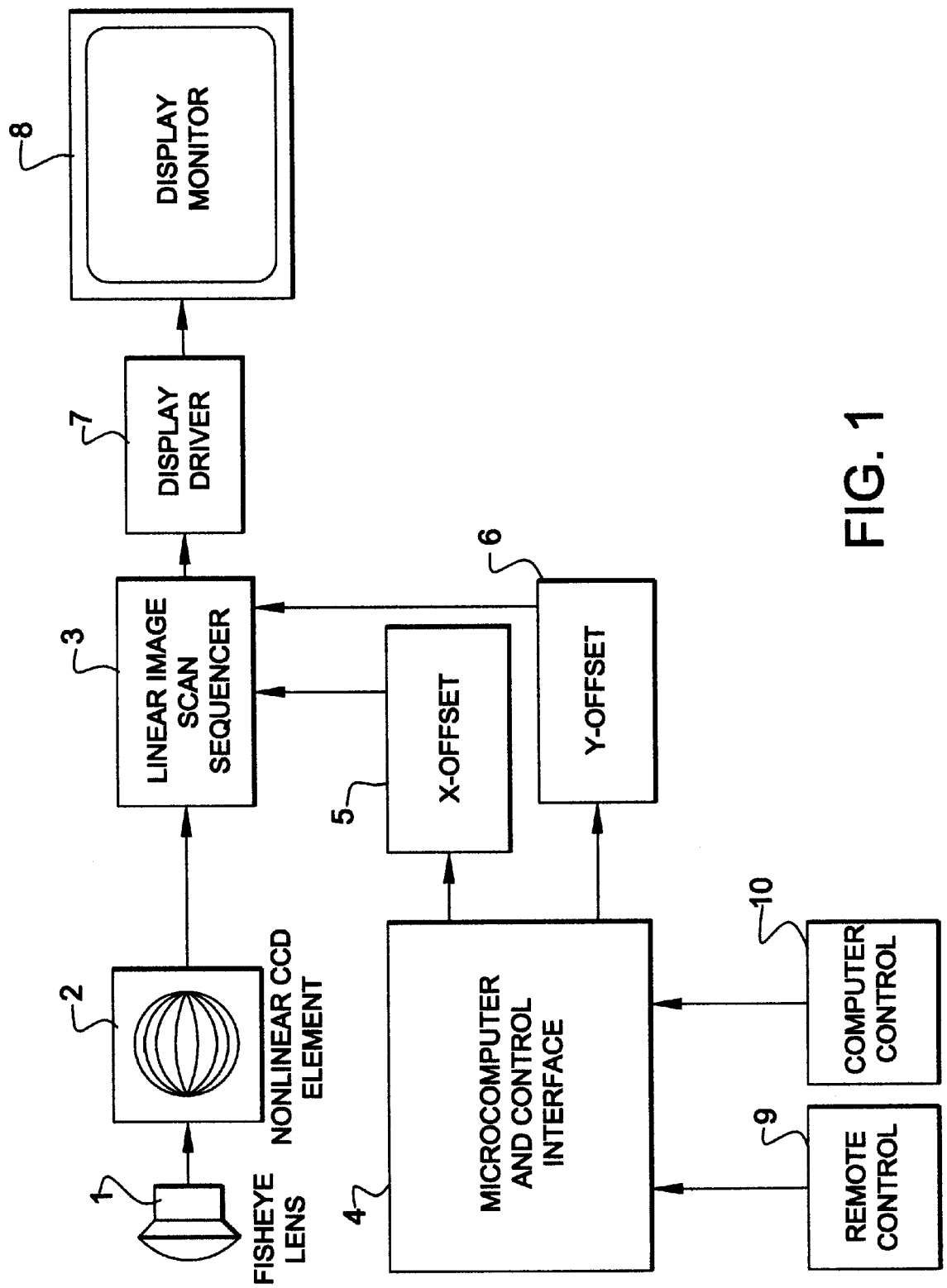
FIG. 1 shows a schematic block diagram of the present invention illustrating the major components thereof for pan and tilt only.
Figure 7:
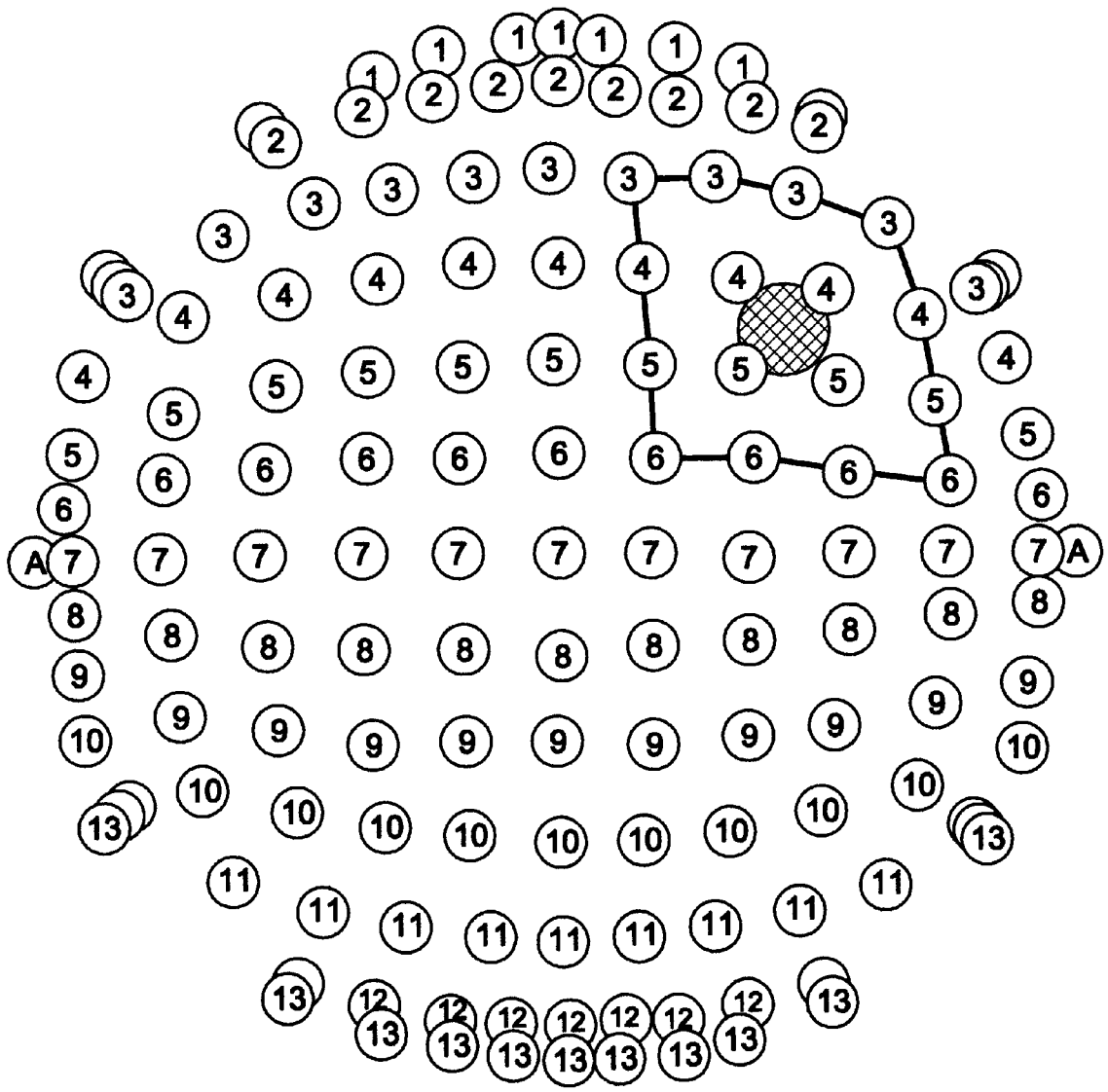
FIG. 7 is a schematic diagram of the geometric layout of the sensing picture elements for the CCD image sensor showing the physical arrangement of a 169 element sensor for a full 180 degree field of view lens. Other numbers of elements and field of view arrangements are supported by this method.

The principles of the present invention can be understood by reference to FIG. 1. Shown schematically at 1 is the fisheye lens that provides an image of the environment with a wide angle field-of-view ranging from 90 to 180 degrees. These lenses are commonly called fisheye lenses due to the distortion that they create in the resulting image. The fisheye lens is attached to a unique charge coupled device (CCD) sensor 2 which converts the optical image into an electrical charge. This sensor is specifically physically arranged to remove the distortion associated with the lens 1 as shown in FIG. 7. These charges are then scanned by a line scan sequencer 3 with an offset determined by user input from a remote control 9 or computer control 10 through a microcontroller interface 4 which sets the x-offset 5 and the y offset 6. Display electronics 7 reconstitutes the scanned image for output to a video display device 8 for viewing.

Figure 4:
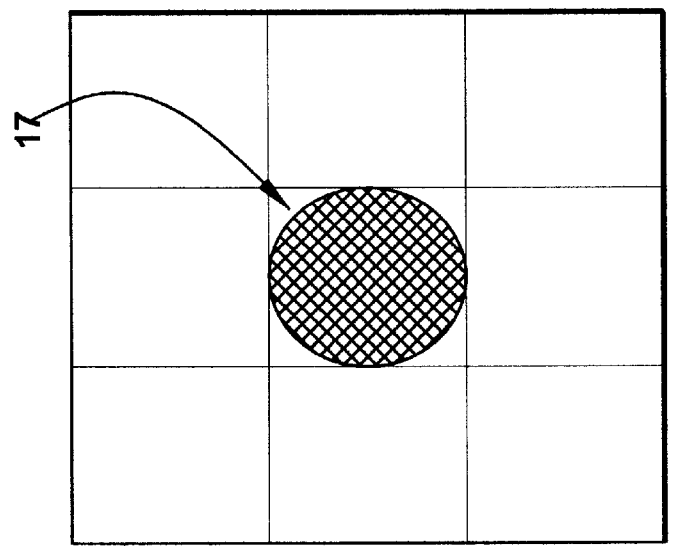
FIG. 4 is an example of the output image after correction for a desired image orientation and magnification within the original image.
Figure 3:
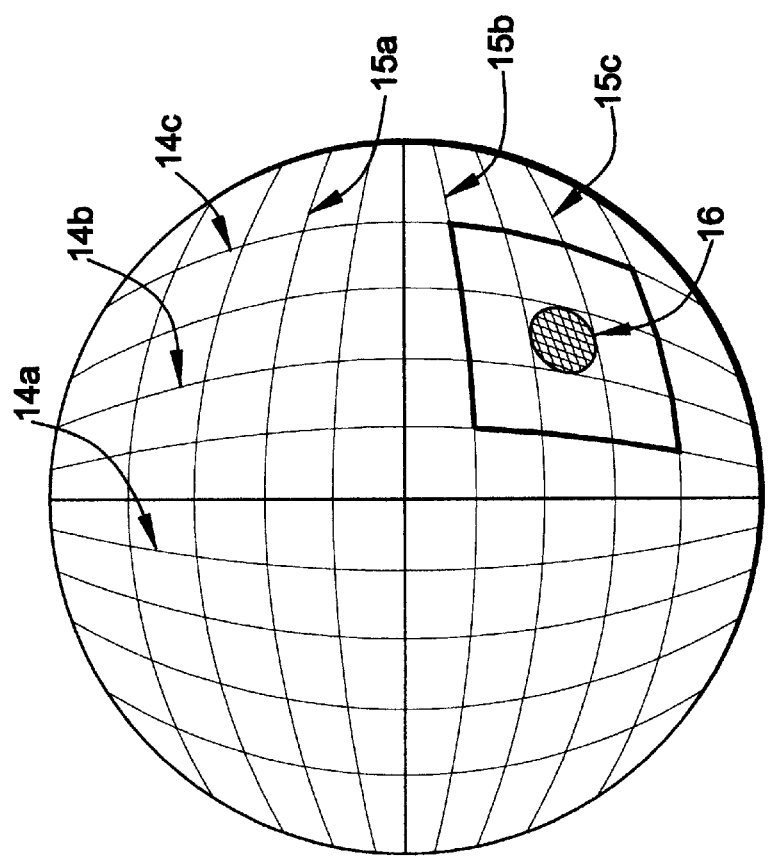
FIG. 3 is an example of a typical fisheye image used as input by the present invention.

The image distortion correction inherent in the fisheye image is corrected by the non-linear arrangement of the CCD elements 2 that allows a linear scan sequencer to scan an image array that is specifically arranged to correct the distortion associated with the lense. The correction that occurs between the input image impinging on the CCD element 2 and the output display driver 7 is better understood by looking at FIG. 3 and FIG. 4. The image shown in FIG. 3 was produced by a fisheye lens. This image has a field-of-view of 180 degrees and shows the contents of the environment throughout an entire hemisphere. While the system is specific to lens field of view, the performance of this approach is in no way limited to only a 180 degree fisheye image. Notice that the resulting image in FIG. 3 is significantly distorted relative to human perception. A portion of the image in FIG. 3 has been correct, magnified, and rotated to produce the image shown in FIG. 4. The results shown in the image in FIG. 4 can be produced from any portion of the image of FIG. 3 using the present invention. In the present invention, these transformations can be performed at real-time video rates (30 times per second), compatible with commercial video standards.

Figure 2:
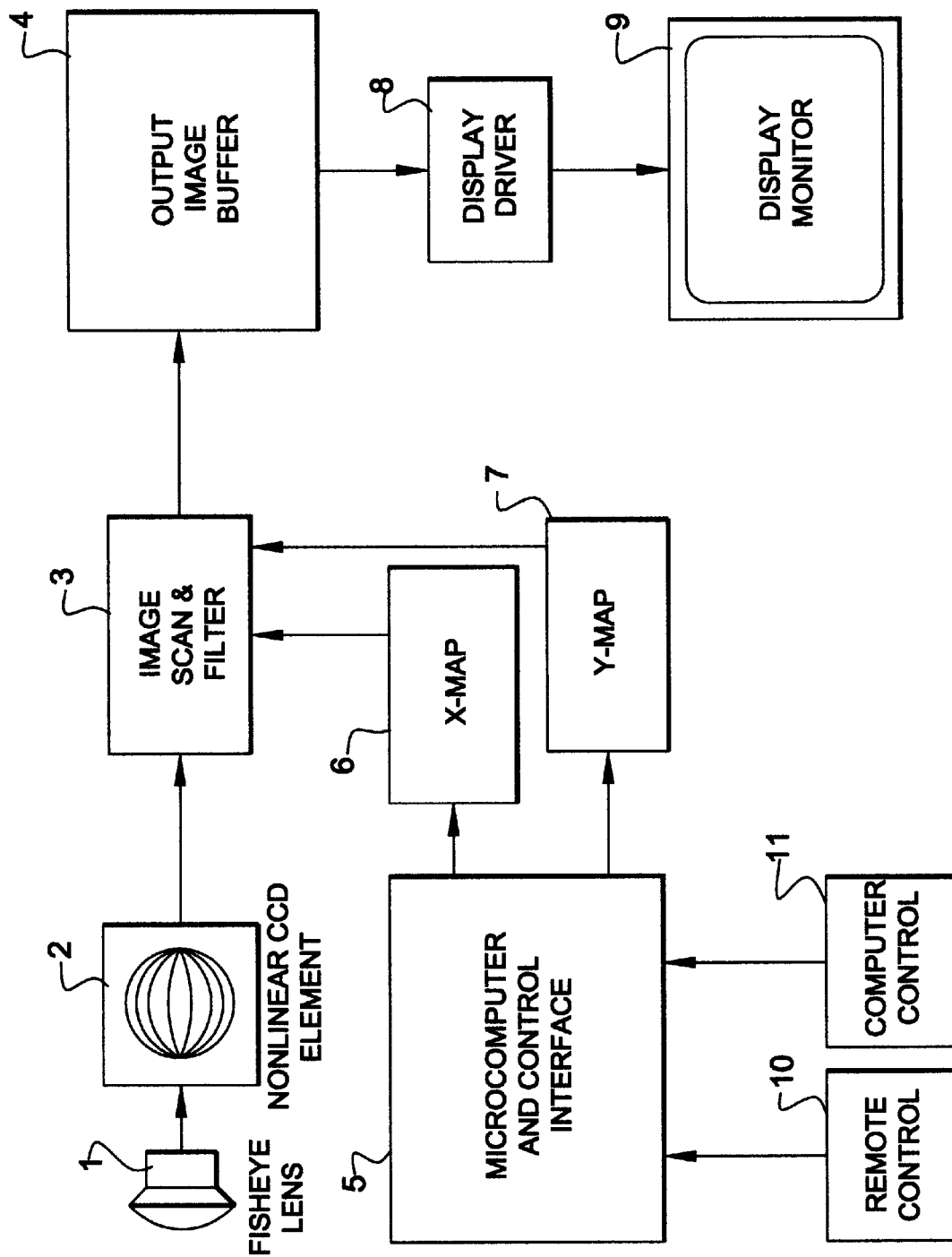
FIG. 2 shows a schematic block diagram of the present invention illustrating the major components thereof for pan, tilt, rotation and magnify.

FIG. 2 is an embodiment that adds the necessary components required to provide image rotation and magnification in addition to pan and tilt capabilities. In this embodiment, the requirement for a pixel by pixel address generator is needed due to the fact that each output scan line crosses multiple input element rows.

The principles of this embodiment can be understood by reference to FIG. 2. Shown schematically at 1 is the fisheye lens that provides an image of the environment with a wide angle field-of-view ranging from 90 to 180 degrees. These lenses are commonly called fisheye lenses due to the distortion that they create in the resulting image. The fisheye lens is attached to a unique charge coupled device (CCD) sensor 2 which converts the optical image into an electrical charge. This sensor is specifically physically arranged to remove the distortion associated with the lens 1 as shown in FIG. 7. These charges are then scanned by an addressable image sequencer 3 with sequencing determined by user input from a remote control 10 or computer control 11 through a microcontroller interface 5 which sets the x-mapping 6 and the y-mapping 7. An output image buffer 4 captures the image for reconstruction. Display driver electronics 8 scan the output buffer to create an image for output to a video display device 9 for viewing.

The image distortion correction inherent in the fisheye image is corrected by the non-linear arrangement of the CCD elements 2 that allows a linear scan sequencer to scan an image array that is specifically arranged to correct the distortion associated with the lens as shown in FIG. 7. The correction that occurs between the input image impinging on the CCD element 2 and the output display driver 7 is better understood by looking at FIG. 3 and FIG. 4. The image shown in FIG. 3 was produced by a fisheye lens. This image has a field-of-view of 180 degrees and shows the contents of the environment throughout an entire hemisphere. While the system is specific to lens field of view, the performance of this approach is in no way limited to only a 180 degree fisheye image. Notice that the resulting image in FIG. 3 is significantly distorted relative to human perception. A portion of the image in FIG. 3 has been corrected, magnified, and rotated to produce the image shown in FIG. 4. The results shown in the image in FIG. 4 can be produced from any portion of the image of FIG. 3 using the present invention. In the present invention, these transformations can be performed at real-time video rates (30 times per second), compatible with commercial video standards.

The postulates and equations that follow are based on the present invention utilizing a fisheye lens as the optical element These equations determine the geometric configuration of the CCD elements to automatically remove the distortions in a wide angle lens. There are two basic properties and two basic postulates that describe the perfect fisheye lens system. The first property of a fisheye lens is that the lens has a $2\pi$ steradian field-of-view and the image it produces is a circle. The second property is that all objects in the field-of-view are in focus, I.e. the perfect fisheye lens has an infinite depth-of-field. The two important postulates of the fisheye lens system are stated as follows:

Postulate 1: Azimuth angle invariability—For object points that lie in a content plane that is perpendicular to the image plane and passes through the image plane origin, all such points are mapped as image points onto the line of intersection between the image plane and the content plane, i.e. along a radial line. The azimuth angle of the image points is therefore invariant to elevation and object distance changes within the content plane.

Postulate 2: Equidistant Projection Rule—The radial distance, r, from the image plane origin along the azimuth angle containing the projection of the object point is linearly proportional to the zenith angle $\beta$, where $\beta$ is defined as the angle between a perpendicular line through the image plane origin and the line from the image plane origin to the object point. Thus the relationship:

$$r = k\beta \tag{1}$$

Figure 5:
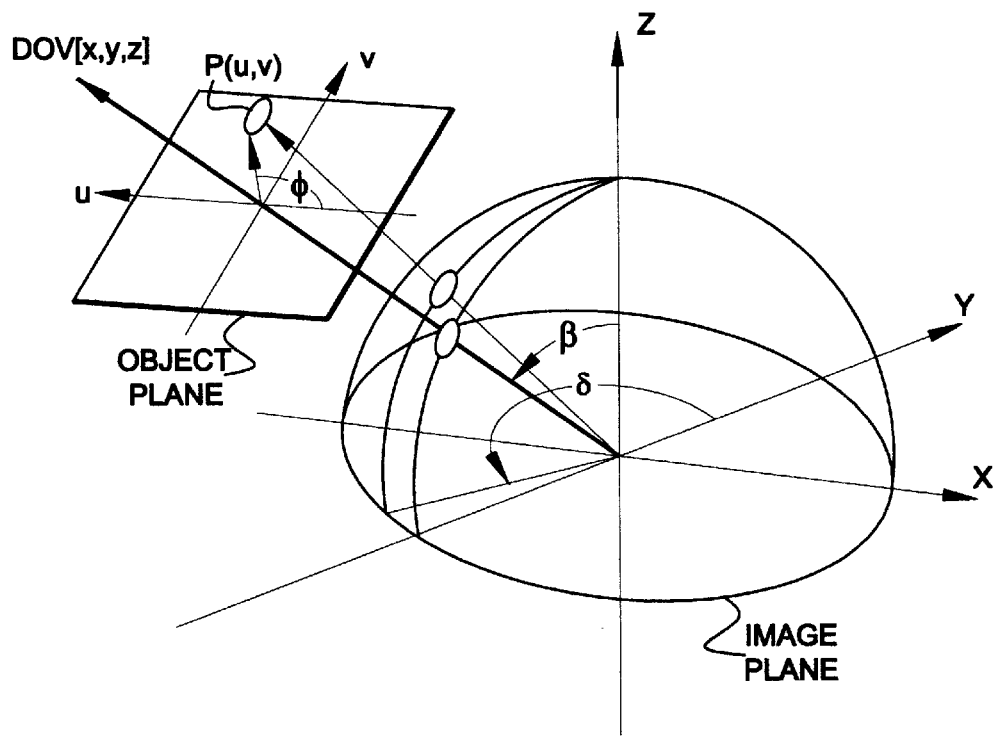
FIG. 5 is a schematic diagram of the fundamental geometry that the present invention embodies to accomplish the image transformation.

Using these properties and postulates as the foundation of the fisheye lens system, the mathetical transformation for obtaining a perspective corrected image can easily be determined. The picture in FIG. 5 shows the coordinate reference frames for the object plane and the image plane. The coordinates u,v describe object points within the object plane. The coordinates x,y,z describe points within the image coordinate frame of reference.

The object plane shown in FIG. 5 is a typical region of interest that we desire to determine the mapping relationship onto the image plane to properly undistort the object. The direction of view vector, DOV[x,y,z], determines the zenith and azimuth angles for mapping the object plane, UV, onto the image plane, XY. The object plane is defined to be perpendicular to the vector, DOV[x,y,z].

The location of the origin of the object plane in terms of the image plane in spherical coordinates is given by:

$$x = D \sin \beta \cos \partial$$
$$y = D \sin \beta \sin \partial$$
$$z = D \cos \beta \tag{2}$$

where D=scalar length from the image plane origin to the object plane origin, $\beta$ is the zenith angle, and $\partial$ is the azimuth angle in image plane spherical coordinates. The origin of object plane is represented as a vector using the components given in equation 1 as:

$$DOV[x,y,z] = [D \sin \beta \cos \partial, D \sin \beta \sin \partial, D \cos \beta] \tag{3}$$

DOV[x,y,z] is perpendicular to the object plane and its scalar magnitude D provides the distance to the object plane. By aligning the YZ plane with the direction of action of DOV[x,y,z], the azimuth angle $\partial$ becomes either 90 or 270 degrees and therefore the x component becomes 0 resulting in the DOV[x,y,z] coordinates:

$$DOV[x,y,z] = [0, -D \sin \beta, D \cos \beta] \tag{4}$$

Figure 6:
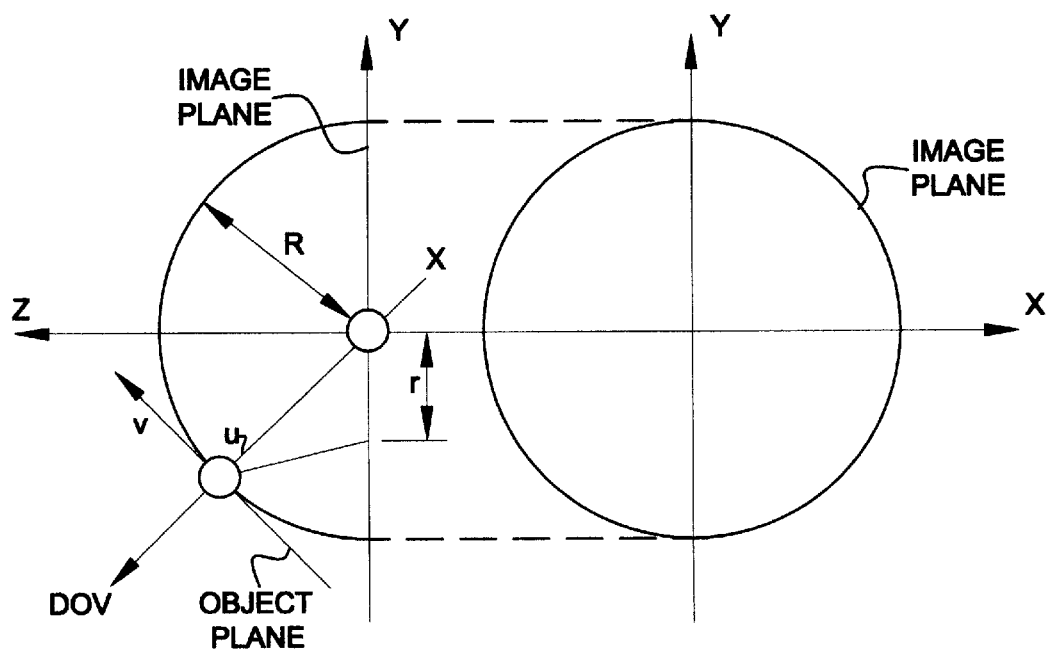
FIG. 6 is a schematic diagram demonstrating the projection of the object plane and position vector into image plane coordinates.

Referring now to FIG. 6, the object point relative to the UV plane origin in coordinates relative to the origin of the image plane is given by the following:

$$x = u$$
$$y = v \cos \beta$$
$$z = v \sin \beta \tag{5}$$

therefore, the coordinates of a point P(u,v) that lies in the object plane can be represented as a vector P[x,y,z] in image plane coordinates:

$$P[x,y,z] = [u, v \cos \beta, v \sin \beta] \tag{6}$$

where P[x,y,z] describes the position of the object point in image coordinates relative to the origin of the UV plane. The object vector that describes the object point in image coordinates is then given by:

$$O[x, y, z] = DOV[x, y, z] + P[x, y, z] \tag{7}$$

$$O[x, y, z] = [u, v \cos \beta - D \sin \beta, v \sin \beta + D \cos \beta] \tag{8}$$

Projection onto a hemisphere of radius R attached to the image plane is determined by scaling the object vector O[x,y,z] to produce a surface vector S[x,y,z]:

$$S[x, y, z] = \frac{RO[x, y, z]}{|O[x, y, z]|} \tag{9}$$

By substituting for the components of O[x,y,z] the vector S[x,y,z] describing the image point mapping onto the hemisphere becomes:

$$S[x, y, z] = \frac{RO[u, (v\cos\beta - D\sin\beta), (v\sin\beta + D\cos\beta)]}{\sqrt{u^2 + (v\cos\beta - D\sin\beta)^2 + (v\sin\beta + D\cos\beta)^2}} \tag{10}$$

The denominator in the last equation represents the length or absolute value of the vector O[x,y,z] and can be simplified through algebraic and trigonometric manipulation to give:

$$S[x, y, z] = \frac{RO[u, (v\cos\beta - D\sin\beta), (v\sin\beta + D\cos\beta)]}{\sqrt{u^2 + v^2 + D^2}} \tag{11}$$

From equation 11, the mapping onto the two-imensional image plane can be obtained for both x and y as:

$$x = \frac{Ru}{\sqrt{u^2 + v^2 + D^2}} \quad (12)$$

$$y = \frac{R(v\cos\beta - D\sin\beta)}{\sqrt{u^2 + v^2 + D^2}} \quad (13)$$

Additionally, the image plane center to object plane distance D can be represented in terms of the fisheye image circular radius R by the relation:

$$D = mR \quad (14)$$

where m represents the scale factor in radial units R from the image plane origin to the object plane origin. Substituting equation 14 into equations 12 and 13 provides a means for obtaining an effective scaling operation or magnification which can be used to provide zoom operation.

$$x = \frac{Ru}{\sqrt{u^2 + v^2 + m^2R^2}} \quad (15)$$

$$y = \frac{R(v\cos\beta - mR\sin\beta)}{\sqrt{u^2 + v^2 + m^2R^2}} \quad (16)$$

Using the equations for two-dimensional rotation of axes for both the UV object plane and the XY image plane the last two equations can be further manipulated to provide a more general set of equations that provides for rotation within the image plane and rotation within the object plane.

$$x = \frac{R[uA - vB + mR\sin\beta\sin\partial]}{\sqrt{u^2 + v^2 + m^2R^2}} \quad (17)$$

$$y = \frac{R[uC - vD - mR\sin\beta\cos\partial]}{\sqrt{u^2 + v^2 + m^2R^2}} \quad (18)$$

where $A = (\cos\emptyset \cos\partial - \sin\emptyset \sin\partial \cos\beta)$ $B = (\sin\emptyset \cos\partial + \cos\emptyset \sin\partial \cos\beta)$ $C = (\cos\emptyset \sin\partial + \sin\emptyset \cos\partial \cos\beta)$ $D = (\sin\emptyset \sin\partial - \cos\emptyset \cos\partial \cos\beta) \quad (19)$ and where R=radius of the image circle
β=zenith angle
∂=Azimuth angle in image plane
Ø=Object plane rotation angle
m=Magnification
u,v=object plane coordinates
x,y=image plane coordinates The equations 17 and 18 provide a direct mapping from the UV space to the XY image space and are the fundamental mathematical result that supports the functioning of the present omnidirectional viewing system with no moving parts. By knowing the desired zenith, azimuth, and object plane rotation angles and the magnification, the locations of x and y in the imaging array can be determined. This approach provides a means to transform an image from the input video buffer to the output video buffer exactly. Also, the fisheye image system is completely symmetrical about the zenith, therefore, the vector assignments and resulting signs of various components can be chosen differently depending on the desired orientation of the object plane with respect ot the image plane. In addition, these postulates and mathematical equations can be modified for various lens elements as necessary for the desired field-of-view coverage in a given application.

The calculations of equations (17), (18), and (19) simplify if image rotation is not allowed (Ø=0) and can be implemented by geometric layout if a specific lens field-of-view is selected and not variable. Equations (20), (21), (22) give the simplified result which can be implemented via a geometric layout for a constant image circle radius R provided by a specific lens:

$$x = \frac{R[uA - vB + mR\sin\beta\sin\partial]}{\sqrt{u^2 + v^2 + m^2R^2}} \quad (20)$$

$$y = \frac{R[uC - vD - mR\sin\beta\cos\partial]}{\sqrt{u^2 + v^2 + m^2R^2}} \quad (21)$$

where $A = \cos\partial$ $B = \sin\partial \cos\beta$ $C = \sin\partial$ $D = -\cos\partial \cos\beta \quad (22)$ and where R=radius of the image circle
β=zenith angle
∂=Azimuth angle in image plane
m=Magnification
u,v=object plane coordinates
x,y=image plane-coordinates FIG. 7 shows the general location of CCD elements that result if the previous equations are implemented for a specific lens configuration and then the elements are positioned to remove the lens distortion by their physical placement. The circled numbers refer to picture elements that are specially positioned for distortion correction. Scan line 1 which would traditionally be horizontally across the top of the device has been repositioned to form a half circle that starts on the "equator" and spans the upper circumference of the element The embodiment will scan this "line" out to the upper scan line on the output image, automatically correcting the distortion associated with the lens. Two special elements marked "A" are overlapping points where each scan begins and ends for the ideal 180 degree fisheye image. By physically implementing the distortion correction, the required mathmatical transformation processing is significantly reduced and in some cases eliminated.

From the foregoing, it can be seen that at least two embodiments of the present invention are presented. In both, a fisheye lens provides a hemispherical view that is captured by a camera. The image is then transformed into a corrected image at a desired pan, tilt, magnification, rotation, and focus based on the desired view as described by a control input The image is then output to a television display with the perspective corrected.

I claim:

1. An electronic imaging system comprising:
a wide-angle lens for producing a wide-angle image, the wide-angle lens producing a perspective distortion in the wide-angle image; and
an imaging sensor, having a surface in optical communication with the wide-angle lens, for generating an output signal representing at least a portion of a corrected wide-angle image, the imaging sensor comprising a plurality of imaging elements, the plurality of imaging elements having a distribution on the surface representable by a nonlinear function,
wherein the plurality of imaging elements are distributed such that the perspective distortion in the wide-angle image is substantially corrected to produce the corrected wide-angle image, at least three of the plurality of imaging elements being distributed to define a first curved row of imaging elements, each of the imaging elements defining the first curved row corresponding to a different point on a first straight line along the corrected wide-angle image,
thereby allowing for direct mapping between the at least three sensor elements and the points on the first straight line in the corrected wide-angle image.

2. The system of claim 1 wherein the plurality of imaging elements are distributed as a two-dimensional array.

3. The system of claim 2 wherein each of the plurality of imaging elements is electronically addressable by a two-dimensional address.

4. The system of claim 1 wherein each of the plurality of imaging elements includes a pixel of a charge-coupled device.

5. The system of claim 1 wherein the output signal is a video signal.

6. The system of claim 1 wherein the output signal includes a plurality of image data.

7. The system of claim 1 further comprising a display for displaying at least a portion of the corrected wide-angle image responsive to the output signal.

8. The system of claim 1 further comprising an image processing unit for selectively magnifying a first region of the corrected wide-angle image responsive to the output signal and a user command signal.

9. The system of claim 8 further comprising an image processing unit for selectively panning from a second region of the corrected wide-angle image to a third region of the corrected wide-angle image responsive to the output signal and a user command signal.

10. The system of claim 8 further comprising a user interface device coupled to the image processing unit for generating the user command signal.

11. A sensor used in an electronic imaging system having a wide-angle lens for producing a wide-angle image having a perspective distortion, the sensor comprising:
a surface in optical communication with the wide-angle lens; and
a plurality of imaging elements, coupled to the surface, for generating an output signal representing at least a portion of a corrected wide-angle image, the plurality of imaging elements having a distribution on the surface representable by a nonlinear function,
wherein the plurality of imaging elements are distributed such that the perspective distortion in the wide-angle image is substantially corrected to produce the corrected wide-angle image, at least three of the plurality of imaging elements being distributed to define a first curved row of imaging elements, each of the imaging elements defining the first curved row corresponding to a different point on a first straight line along the corrected wide-angle image.
thereby allowing for direct mapping between the at least three sensor elements and the points on the first straight line in the corrected wide-angle image.

12. The sensor of claim 11 wherein the plurality of imaging elements are distributed as a two-dimensional array.

13. The sensor of claim 12 wherein each of the plurality of imaging elements is electronically addressable by a two-dimensional address.

14. The sensor of claim 11 wherein each of the plurality of imaging elements includes a pixel of a charge-coupled device.

15. The sensor of claim 11 wherein the output signal is a video signal.

16. The sensor of claim 11 wherein the output signal includes a plurality of image data.

17. A processing terminal comprising:
a wide-angle lens for producing a wide-angle image, the wide-angle lens producing a perspective distortion in the wide-angle image; and
an imaging sensor, having a surface in optical communication with the wide-angle lens, for generating an output signal representing at least a portion of a corrected wide-angle image, the imaging sensor comprising a plurality of imaging elements, the plurality of imaging elements having a distribution on the surface representable by a nonlinear function,
wherein the plurality of imaging elements are distributed such that the perspective distortion in the wide-angle image is substantially corrected to produce the corrected wide-angle image, at least three of the plurality of imaging elements being distributed to define a first curved row of imaging elements, each of the imaging elements defining the first curved row corresponding to a different point on a first straight line along the corrected wide-angle image;
thereby allowing for direct mapping between the at least three sensor elements and the points on the first straight line in the corrected wide-angle image.

18. A processing terminal configured to be used with a wide-angle lens, the processing terminal comprising:
a surface, in optical communication with the wide-angle lens, configured to receive a wide-angle image having a perspective distortion associated with the wide-angle lens; and
a plurality of imaging elements, coupled to the surface, for generating an output signal representing at least a portion of a corrected wide-angle image, the plurality of imaging elements having a distribution on the surface representable by a nonlinear function,
wherein the plurality of imaging elements are distributed such that the perspective distortion in the wide-angle image is substantially corrected to produce the corrected wide-angle image, at least three of the plurality of imaging elements being distributed to define a first curved row of imaging elements, each of the imaging elements defining the first curved row corresponding to a different point on a first straight line along the corrected wide-angle image.
thereby allowing for direct mapping between the at least three sensor elements and the points on the first straight line in the corrected wide-angle image.

19. The electronic imaging system of claim 1, further including a second curved row of imaging elements at least partially different from the first curved row of imaging elements, the second curved row of imaging elements being defined by at least three of the plurality of imaging elements, each of the imaging elements defining the second curved row corresponding to a different point on a second straight line along the corrected wide-angle image different from the first straight line.

20. The sensor of claim 11, further including a second curved row of imaging elements at least partially different from the first curved row of imaging elements, the second curved row of imaging elements being defined by at least three of the plurality of imaging elements, each of the imaging elements defining the second curved row corresponding to a different point on a second straight line along the corrected wide-angle image different from the first straight line.

21. The processing terminal of claim 17, further including a second curved row of imaging elements at least partially different from the first curved row of imaging elements, the second curved row of imaging elements being defined by at least three of the plurality of imaging elements, each of the imagging elements defining the second curved row corresponding to a different point on a second straight line along the corrected wide-angle image different from the first straight line.

22. The processing terminal of claim 18, further including a second curved row of imaging elements at least partially different from the first curved row of imaging elements, the second curved row of imaging elements being defined by at least three of the plurality of imaging elements, each of the imaging elements defining the second curved row corresponding to a different point on a second straight line along the corrected wide-angle image different from the first straight line.

23. A sensor configured to optically receive a wide-angle image, the wide-angle image having a perspective distortion associated with a wide-angle lens, the sensor comprising a plurality of imaging elements nonlinearity distributed in space, at least three of the plurality of imaging elements being distributed in space so as to define a first curved row of imaging elements, each of the at least three imaging elements defining the first curved row corresponding to a different point on a first straight line along a corrected wide-angle image, the corrected wide-angle image being the wide-angle image substantially without the perspective distortion, thereby allowing for direct mapping between the at least three sensor elements and the points on the first straight line in the corrected wide-angle image.

24. The sensor of claim 23, further including a second curved row of imaging elements at least partially different from the first curved row of imaging elements, the second curved row of imaging elements being defined by at least three of the plurality of imaging elements, each of the imaging elements defining the second curved row corresponding to a different point on a second straight line along the corrected wide-angle image different from the first straight line.

25. The sensor of claim 24, wherein a set of the image elements defining the first curved row and a set of the imaging elements defining the second curved row comprise two different imaging elements in common.

26. The sensor of claim 25, wherein the two different imaging elements are diametrically opposed.

27. The sensor of claim 23, wherein the plurality of imaging elements are distributed as a two-dimensional array.

28. The sensor of claim 23, wherein the sensor is configured to generate a signal representing at least a portion of the corrected wide-angle image.

29. The sensor of claim 23, wherein sensor is configured to receive a plurality of wide-angle images over time each having the distortion, the sensor being configured to generate a signal representing at least a portion of each of a plurality of corrected wide-angle images over time, each of the corrected wide-angle images comprising one of the plurality of wide-angle images substantially without the distortion.

30. The sensor of claim 29, wherein the signal represents the at least a portion of each of the plurality of corrected wide-angle images at a real-time video rate.

31. The sensor of claim 30, wherein the real-time video rate is about 30 images per second.

32. The sensor of claim 23, wherein the sensor comprises a charge-coupled device, and wherein each of the plurality of imaging elements comprises a picture element of the charge-couple device.

33. A method comprising:
optically receiving at a sensor a wide-angle image, the wide-angle image having a perspective distortion associated with a wide-angle lens, the sensor comprising a plurality of imaging elements nonlinearity distributed in space, at least three of the plurality of imaging elements being distributed in space so as to define a first curved row of imaging elements, each of the imaging elements defining the first curved row corresponding to a different point on a first straight line along a corrected wide-angle image, the corrected wide-angle image being the wide-angle image substantially without the perspective distortion; and generating a signal representing at least a portion of the corrected wide-angle image by directly mapping between the at least three sensor elements and the points on the first straight line in the corrected wide-angle image.

34. The method of claim 33, wherein the step of generating the signal comprises the steps of:
scanning at least a portion of the first curved row of imaging elements; and
scanning at least a portion of a second curved row of imaging elements at least partially different from the first curved row of imaging elements, the second curved row of imaging elements being defined by at least three of the plurality of imaging elements, each of the imaging elements defining the second curved row corresponding to a different point on a second straight line along the corrected wide-angle image different from the first straight line.

35. The method of claim 34, wherein a set of the imaging elements defining the first curved row and a set of the imaging elements defining the second curved row comprise two different imaging elements in common.

36. The method of claim 35, wherein the two different imaging elements are diametrically opposed.

* * * * *